United States Patent
Patil et al.

(10) Patent No.: US 10,738,259 B2
(45) Date of Patent: Aug. 11, 2020

(54) NAPHTHALENE-1,8-DICARBOXYLATE ESTER COMPOUNDS AND LUBRICATING OIL BASE STOCKS AND PROCESSES FOR MAKING SAME

(71) Applicant: ExxonMobil Chemical Patents Inc., Baytown, TX (US)

(72) Inventors: Abhimanyu O. Patil, Westfield, NJ (US); Hong Cheng, Bridgewater, NJ (US); Stephen T. Cohn, Spring, TX (US); James R. Lattner, La Porte, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 17 days.

(21) Appl. No.: 16/012,830

(22) Filed: Jun. 20, 2018

(65) Prior Publication Data

US 2019/0048280 A1  Feb. 14, 2019

Related U.S. Application Data

(60) Provisional application No. 62/542,395, filed on Aug. 8, 2017.

(30) Foreign Application Priority Data

Oct. 19, 2017  (EP) .................... 17197191

(51) Int. Cl.
*C10M 105/36* (2006.01)
*C07C 69/94* (2006.01)
*C07C 67/08* (2006.01)
*C07C 69/76* (2006.01)

(52) U.S. Cl.
CPC .......... *C10M 105/36* (2013.01); *C07C 67/08* (2013.01); *C07C 69/76* (2013.01); *C07C 69/94* (2013.01); *C10M 2207/2855* (2013.01); *C10N 2220/022* (2013.01); *C10N 2240/10* (2013.01)

(58) Field of Classification Search
CPC ......... C07C 69/00; C07C 67/08; C07C 69/94; C10N 2220/022; C10N 2240/10; C10M 2207/2855

See application file for complete search history.

(56) References Cited

U.S. PATENT DOCUMENTS

| | | | |
|---|---|---|---|
| 3,719,466 A | 3/1973 | Ahle | |
| 6,113,931 A * | 9/2000 | Bonda | A61K 8/35 424/400 |
| 6,355,261 B1 * | 3/2002 | Bonda | A61Q 19/02 424/401 |
| 8,779,084 B2 * | 7/2014 | Liu | C08G 63/672 528/272 |
| 2002/0081272 A1 * | 6/2002 | Guenin | A61K 8/0229 424/65 |
| 2004/0247543 A1 * | 12/2004 | Huerta | A61K 8/27 424/59 |
| 2007/0197408 A1 | 8/2007 | Holt | |
| 2008/0051307 A1 | 2/2008 | Li | |
| 2014/0179845 A1 * | 6/2014 | Dakka | C07C 69/24 524/286 |
| 2017/0183595 A1 | 6/2017 | Ng et al. | |

FOREIGN PATENT DOCUMENTS

| | | |
|---|---|---|
| EP | 2726584 | 5/2014 |
| KR | 2016-0082897 | 7/2016 |

OTHER PUBLICATIONS

U.S. Appl. No. 15/913,985, filed Mar. 7, 2018 Ng et al.

* cited by examiner

*Primary Examiner* — Vishal V Vasisth

(57) ABSTRACT

This disclosure relates to naphthalene-1,8-dicarboxylate ester compounds, lubricating oil base stocks comprising naphthalene-1,8-dicarboxylate ester compounds, lubricating oil compositions comprising such base stocks, and method of making such base stocks. The lubricating oil base stocks comprising naphthalene-1,8-dicarboxylate ester compounds exhibit desirable lubricating properties such as polarity.

15 Claims, No Drawings

NAPHTHALENE-1,8-DICARBOXYLATE ESTER COMPOUNDS AND LUBRICATING OIL BASE STOCKS AND PROCESSES FOR MAKING SAME

PRIORITY

This application claims priority to and the benefit of U.S. Provisional Application No. 62/542,395, filed Aug. 8, 2017, and EP 17197191.4 which was filed Oct. 19, 2017, the disclosures of both of which are incorporated herein by reference in their entirety.

FIELD OF THE DISCLOSURE

This disclosure relates to naphthalene-1,8-dicarboxylate esters, lubricating oil base stocks, and lubricating oil compositions. In particular, this disclosure relates to naphthalene-1,8-dicarboxylate ester compounds, and lubricating oil base stocks and lubricating oil formulations comprising naphthalene-1,8-dicarboxylate ester compounds.

BACKGROUND OF THE DISCLOSURE

Lubricants in commercial use today are prepared from a variety of natural and synthetic base stocks admixed with various additive packages and solvents depending upon their intended application. The base stocks typically include mineral oils, polyalphaolefins (PAO), gas-to-liquid (GTL) base oils, silicone oils, phosphate esters, diesters, polyol esters, and the like.

A major trend for passenger car engine oils (PCEOs) is an overall improvement in quality as higher quality base stocks become more readily available. Typically the highest quality PCEO products are formulated with base stocks such as PAOs or GTL stocks admixed with various additive packages.

Polyalpha-olefins (PAOs) are important lube base stocks with many excellent lubricant properties, including high viscosity index (VI), low volatility and are available in various viscosity ranges (e.g., kinematic viscosity at 100° C. in the range of 2 to 300 cSt). However, PAOs are paraffinic hydrocarbons with low polarity. This low polarity leads to low solubility and dispersancy for polar additives or sludge generated during service. To compensate for this low polarity, lube formulators usually add one or multiple polar co-base stocks. Ester or alkylated naphthalene (AN) is usually present at 1 to 50 wt % levels in many finished lubricant formulations to increase the fluid polarity which improves the solubility of polar additives and sludge.

Therefore, there is a need for polar base stock fluids that provide appropriate solubility and dispersibility for polar additives or sludge generated during service of lubricating oils.

The present invention meets this and other needs.

SUMMARY OF THE DISCLOSURE

It has been found that naphthalene-1,8-dicarboxylate esters can be advantageously used as lubricating oil base stocks with desirable lubricating oil properties such as polarity.

A first aspect of the present disclosure relates to a lubricating oil base stock comprising a compound having the following formula (F-I):

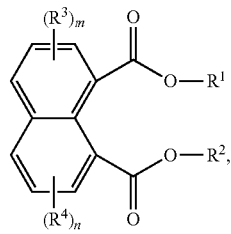

(F-I)

wherein: $R^1$ and $R^2$ are each independently a C1 to C32 linear or branched alkyl group; $R^3$ and $R^4$ are independently at each occurrence a C1 to C20 alkyl group; and m and n are independently 0, 1, 2, or 3.

A second aspect of the present disclosure relates to a lubricating oil formulation comprising a lubricating oil base stock of the first aspect of the present disclosure.

A third aspect of the present disclosure relates to compound having the following formula (F-III):

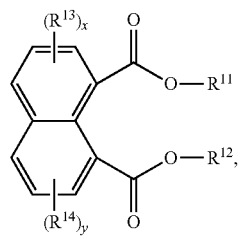

(F-III)

wherein: $R^{11}$ and $R^{12}$ are each independently a C1 to C32 linear or branched alkyl group, and at least one of $R^{11}$ and $R^{12}$ is a group represented by the following formula (F-IV):

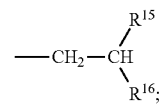

(F-IV)

where $R^{15}$ and $R^{16}$ are each independently a C1-C29 linear or branched alkyl group, and $R^{11}$ and $R^{12}$ can be the same or different when both $R^{11}$ and $R^{12}$ are represented by formula (F-IV); $R^{13}$ and $R^{14}$ are independently at each occurrence a C1 to C20 alkyl group; and x and y are independently 0, 1, 2, or 3.

A fourth aspect of the present disclosure relates to a method for making a lubricating oil base stock comprising a compound having the following formula (F-I):

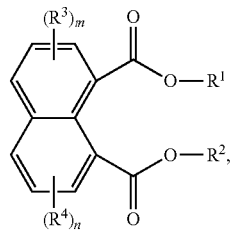

(F-I)

wherein: $R^1$ and $R^2$ each are independently a C1 to C32 linear or branched alkyl group; $R^3$ and $R^4$ are each independently at each occurrence a C1 to C20 alkyl group, and m and n are independently 0, 1, 2, or 3, the method comprising: reacting an acid having a formula (F-V) and/or an anhydride having a formula (F-VI) below with one or more alcohols having a formula $R^1$—OH and/or $R^2$—OH in the presence of a catalyst to obtain a reaction mixture:

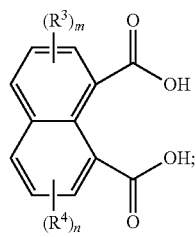
(F-V)

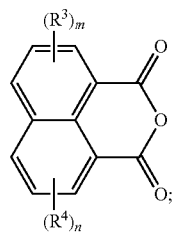
(F-VI)

and obtaining at least a portion of the lubricating oil base stock from the reaction mixture.

Further objectives, features and advantages of the present disclosure will be understood by reference to the following drawings and detailed description.

DETAILED DESCRIPTION OF THE DISCLOSURE

Definitions

In the present disclosure, the indefinite article "a" or "an" means at least one, unless it is clearly specified or indicated by the context to mean one.

"Alkyl group" refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms. "Cycloalkyl group" refers to an alkyl group in which all carbon atoms form a ring structure comprising one or more rings.

"Hydrocarbyl group" refers to a group consisting of hydrogen and carbon atoms only. A hydrocarbyl group can be saturated or unsaturated, linear or branched, cyclic or acyclic, aromatic or non-aromatic.

"Cn" group or compound refers to a group or a compound comprising carbon atoms at total number thereof of n. Thus, "Cm-Cn" or "Cm to Cn" group or compound refers to a group or compound comprising carbon atoms at a total number thereof in the range from m to n. Thus, a "C1-C50 alkyl group" or "C1 to C50 alkyl group" refers to an alkyl group comprising carbon atoms at a total number thereof in the range from 1 to 50.

"Mono-ester" refers to a compound having one ester (—C(O)—O—) functional group therein.

"Di-ester" refers to a compound having two ester (—C(O)—O—) functional groups therein.

"Naphthalene-1,8-dicarboxylate" refers to a di-ester having the following formula:

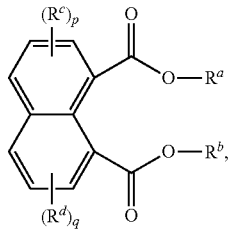

where $R^a$, $R^b$, $R^c$, and $R^d$ are independently substituted or unsubstituted hydrocarbyl groups, and p and q are independently 0, 1, 2, or 3.

The term "Guerbet alcohol" refer to beta-branched alcohol having a structure corresponding to the following formula:

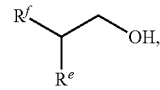

where $R^e$ and $R^f$ are independently linear, branched, cyclic, substituted or unsubstituted hydrocarbyl groups preferably comprising from c1 to c2 carbon atoms, where c1 and c2 can be, independently, 1, 2, 3, 4, 5, 6, 7, 8, 9, 10, 15, 20, 25, 30, 35, 40, 45, 50, 55, 60, 65, 70, 75, 80, 85, 90, 95, or 100, as long as c1<c2. More preferably c1=2 and c2=50. Preferably $R^e$ and $R^f$ are alkyl groups. More preferably $R^e$ and $R^f$ are linear or branched alkyl groups.

"SAE" refers to SAE International, formerly known as Society of Automotive Engineers, which is a professional organization that sets standards for internal combustion engine lubricating oils.

"SAE J300" refers to the viscosity grade classification system of engine lubricating oils established by SAE, which defines the limits of the classifications in rheological terms only.

"Lubricating oil" refers to a substance that can be introduced between two or more surfaces and lowers the level of friction between two adjacent surfaces moving relative to each other. A lubricating oil "base stock" is a material, typically a fluid at various levels of viscosity at the operating temperature of the lubricating oil, used to formulate a lubricating oil by admixing with other components. Non-limiting examples of base stocks suitable in lubricating oils include API Group I, Group II, Group III, Group IV, and Group V base stocks. If one base stock is designated as a primary base stock in the lubricating oil, any additional base stock may be called a co-base stock.

All kinematic viscosity values in the present disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in the present disclosure are as determined pursuant to ASTM D2270.

All Noack volatility ("NV") values in the present disclosure were measured by thermogravimetric analysis ("TGA") based Noack or are as determined pursuant to ASTM D5800 unless specified otherwise. The unit of all NV values is wt %, unless otherwise specified.

All percentages in describing chemical compositions herein are by weight unless specified otherwise. "Wt %" means percent by weight.

"Consisting essentially of" means comprising at a concentration by weight of at least 90 wt %, based on the total weight of the mixture in question. Thus, a lubricating oil base stock consisting essentially of a given ester compound comprises that ester compound at a concentration by weight of at least 90 wt %, based on the total weight of the lubricating oil base stock.

All numerical values within the detailed description and the claims herein are modified by "about" or "approximately" the indicated value, taking into account experimental error and variations that would be expected by a person having ordinary skill in the art.

I. The Novel Naphthalene-1,8-Dicarboxylate Ester Compounds

One aspect of the present disclosure is a novel category of compounds having a general formula (F-III) below:

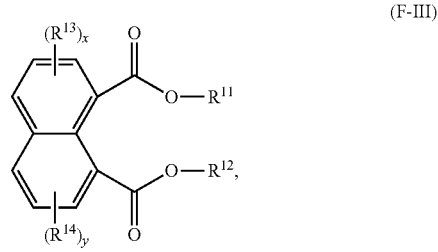

wherein:
$R^{11}$ and $R^{12}$ are independently C1-C32 linear or branched alkyl groups, and at least one of $R^{11}$ and $R^{12}$ is a group represented by the following formula (F-IV):

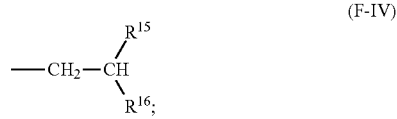

where $R^{15}$ and $R^{16}$ are each independently a C1-C29 linear or branched alkyl group, and $R^{11}$ and $R^{12}$ can be the same or different when both $R^{11}$ and $R^{12}$ are represented by formula (F-IV);

$R^{13}$ and $R^{14}$ are independently at each occurrence a C1-C20 alkyl group; and x and y are independently 0, 1, 2, or 3, preferably x and y are independently 0 or 1, more preferably x and y are both zero. Where x and y are zero, the naphthalene ring is not substituted at any position other than positions 1 and 8.

In the above formula (F-III), $R^{13}$ denotes a substituent attached to the upper benzene ring of the naphthalene ring at any location available, and $R^{14}$ denotes a substituent attached to the lower benzene ring of the naphthalene ring at any location available. $R^{13}$ and $R^{14}$ can be independently at each occurrence the following: methyl, ethyl, propyl, iso-propyl, n-butyl, 1-methylpropyl, 2-methylpropyl, and the following groups and branched, isomeric variations thereof: n-pentyl; n-hexyl; n-heptyl; n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-icosyl. Preferably $R^{13}$ and $R^{14}$ are independently linear alkyl groups or a 1-methylalkyl group. Preferably $R^{13}$ and $R^{14}$ independently contains 1, 2, 3, 4, 5, 6, 8, 10, 12, 14, 16, 18, or 20 carbon atoms. Where x or y is larger than 1, the multiple $R^{13}$ can be the same or different, and the multiple $R^{14}$ can be the same or different as well.

$R^{11}$ and $R^{12}$ can be the same or different. Preferably $R^{11}$ and $R^{12}$ are identical. Where $R^{11}$ and $R^{12}$ are different, in a preferred embodiment one of $R^{11}$ and $R^{12}$ is a linear alkyl group and the other is a branched alkyl group represented by formula (F-IV).

$R^{11}$ and $R^{12}$ can be independently C1-C32 alkyl groups, preferably at least one of $R^{11}$ and $R^{12}$ is a C8-C24 alkyl group. More preferably both $R^{11}$ and $R^{12}$ are C8-C24 alkyl groups.

Preferably $R^{15}$ and $R^{16}$ are each independently a C2-C22 linear or branched alkyl group. More preferably $R^{15}$ and $R^{16}$ are each independently a C2-C22 linear alkyl group. Still more preferably the difference in total number of carbon atoms contained in $R^{15}$ and $R^{16}$ is two (2). Preferably, $R^{15}$ and $R^{16}$ contain even numbers of carbon atoms.

The novel naphthalene-1,8-dicarboxylate ester compounds as an aspect of the present disclosure can be advantageously used as a lubricating oil base stock, a heat transfer oil (e.g., transformer oil), a hydraulic power transfer oil, a processing oil, a plasticizer, and the like.

Particularly desirable examples of the naphthalene-1,8-dicarboxylate ester compounds are as follows:
bis(2-ethylhexyl) naphthalene-1,8-dicarboxylate;
bis(2-butyloctyl) naphthalene-1,8-dicarboxylate;
bis(2-hexyldecyl) naphthalene-1,8-dicarboxylate;
bis(2-octyldocecyl) naphthalene-1,8-dicarboxylate;
bis(2-decyltetradecyl) naphthalene-1,8-dicarboxylate;
2-ethylhexyl 2-butyloctyl naphthalene-1,8-dicarboxylate;
2-ethylhexyl 2-hexyldecyl naphthalene-1,8-dicarboxylate;
2-ethylhexyl 2-octyldodecyl naphthalene-1,8-dicarboxylate;
2-ethylhexyl 2-decyltetradecyl naphthalene-1,8-dicarboxylate;
2-butyloctyl 2-hexyldecyl naphthalene-1,8-dicarboxylate;
2-butyloctyl 2-octyldodecyl naphthalene-1,8-dicarboxylate;
2-butyloctyl 2-decyltetradecyl naphthalene-1,8-dicarboxylate;
2-hexyldecyl 2-octyldodecyl naphthalene-1,8-dicarboxylate;
2-hexyldecyl 2-decyltetradecyl naphthalene-1,8-dicarboxylate; and
2-octyldodecyl 2-decyltetradecyl naphthalene-1,8-dicarboxylate.

II. Naphthalene-1,8-dicarboxylate Ester Base Stocks

II.1 General

In a surprising manner, the present inventors found that naphthalene-1,8-dicarboxylates have desirable properties such as KV100, KV40, and viscosity index comparable to certain commercial Group V ester-type base stocks. The high polarity of the naphthalene-1,8-dicarboxylate molecules as a result of the presence of the naphthalene ring and the two ester groups lends them excellent blending capabilities with many other base stocks, providing needed solvency and dispersancy of polar components such as additives and sludge formed during the service life of the lubricating oil.

The naphthalene-1,8-dicarboxylate ester base stock of the present disclosure comprises an ester compound having the following (F-I):

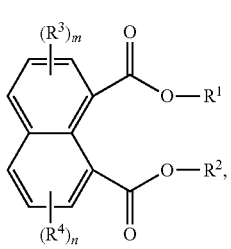

(F-I)

wherein:

$R^1$ and $R^2$ are each independently a C1-C32 linear or branched alkyl group;

$R^3$ and $R^4$ are independently at each occurrence a C1-C20 alkyl group; and m and n are independently 0, 1, 2, or 3, preferably m and n are independently 0 or 1, more preferably m and n are both zero. Where m and n are zero, the naphthalene ring is not substituted in any position other than positions 1 and 8.

In the above formula (F-I), $R^3$ denotes a substituent attached to the upper benzene ring of the naphthalene ring at any location available, and $R^4$ denotes a substituent attached to the lower benzene ring of the naphthalene ring at any location available. $R^3$ and $R^4$ can be independently at each occurrence the following: methyl, ethyl, propyl, isopropyl, n-butyl, 1-methylpropyl, 2-methylpropyl, and the following groups and branched, isomeric variations thereof: n-pentyl; n-hexyl; n-heptyl; n-octyl; n-nonyl; n-decyl, n-undecyl, n-dodecyl, n-tridecyl, n-tetradecyl, n-pentadecyl, n-hexadecyl, n-heptadecyl, n-octadecyl, n-nonadecyl, and n-icosyl. Preferably $R^3$ and $R^4$ are independently linear alkyl groups or a 1-methylalkyl group. Preferably $R^3$ and $R^4$ independently contains 1, 2, 3, 4, 5, 6, 8, 10, 12, 14, 16, 18, 20 carbon atoms.

$R^1$ and $R^2$ are the same or different. Preferably $R^1$ and $R^2$ are identical. Such ester of formula (F-I) where $R^1$ and $R^2$ are identical can be conveniently fabricated by the esterification reaction of a single alcohol. It is possible to make a mixture of multiple ester compounds having different formula (F-I) using more than one naphthalene-1,8-dicarboxylic acid and/or anhydride to react with a single or more alcohols in a single reaction system. It is also possible to make a mixture of multiple compounds having different formula (F-I) using the acid and/or anhydride of a single naphthalene-1,8-dicarboxylic acid to react with at least two different alcohols. It is also possible to make a mixture of multiple compounds having different formula (F-I) using the acid and/or anhydride of multiple naphthalene-1,8-dicarboxylic acids to react with at least two different alcohols. Depending on the process of fabricating the lubricating base stock of the present disclosure, one can obtain a base stock comprising one pure ester compound of formula (F-I), or a mixture of multiple ester compounds of formula (F-I).

$R^1$ and $R^2$ can each independently comprise 1 to 32 carbon atoms. Preferably at least one of $R^1$ and $R^2$ is a C8-C24 linear or branched alkyl group. Preferably both $R^1$ and $R^2$ are C8-C24 linear or branched alkyl group. Preferably at least one of $R^1$ and $R^2$ is a linear alkyl group. Preferably both $R^1$ and $R^2$ are linear alkyl groups. Preferably $R^1$ and $R^2$ are both C8-C24 linear or branched alkyl groups having even number of carbon atoms.

In one preferred embodiment, in formula (F-I), $R^1$ and $R^2$ are the same or different, and at least one of $R^1$ and $R^2$ is a branched alkyl group represented by the following formula (F-II):

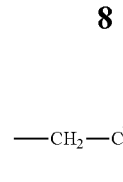

(F-II)

where $R^5$ and $R^6$ are each independently a C1-C29 linear or branched alkyl group. In such embodiment, it is further preferred that $R^5$ and $R^6$ are linear alkyl groups. The difference in total number of carbon atoms in $R^5$ and $R^6$ may preferably be two (2).

Preferably, both $R^1$ and $R^2$, the same or different, independently are represented by formula (F-II) above (i.e., the $R^5$ and $R^6$ in $R^1$ may be the same or different from those in $R^2$).

In another preferred embodiment, in formula (F-I), $R^1$ is a linear alkyl group, and $R^2$ is a branched alkyl group represented by formula (F-II) above. In such embodiments, it is further preferred that both $R^5$ and $R^6$ are linear alkyl groups.

In one particularly advantageous embodiment, the lubricating oil base stock of the present disclosure consists essentially of compounds having a formula (F-I) where both $R^1$ and $R^2$ are independently C1-C32 linear alkyl groups, and more preferably C8-C24 linear alkyl groups. Preferably, $R^1$ and $R^2$ are identical.

In one particularly advantageous embodiment, the lubricating oil base stock of the present disclosure consists essentially of compounds having a formula (F-I) where both $R^1$ and $R^2$ are C1-C32 branched alkyl groups represented by formula (F-II) above, more preferably those in which $R^5$ and $R^6$ are linear alkyl groups. Preferably $R^1$ and $R^2$ are C8-C24 alkyl groups. Preferably $R^1$ and $R^2$ are identical.

In another embodiment, the lubricating oil base stock of the present disclosure comprises a mixture of (i) ester compounds having a formula (F-I) where both $R^1$ and $R^2$ are linear alkyl groups, preferably C8-C24 alkyl groups, more preferably identical alkyl groups, and (ii) ester compounds having a formula (F-I) where both $R^1$ and $R^2$ are branched alkyl groups represented by formula (F-II), preferably C8-C24 alkyl groups, more preferably identical alkyl groups, where $R^5$ and $R^6$ are preferably linear alkyl groups, preferably having a difference in carbon atom number of two (2).

The lubricating oil base stock of the present disclosure can advantageously comprise one or more of the following di-ester compounds:

dioctyl naphthalene-1,8-dicarboxylate;
didecyl naphthalene-1,8-dicarboxylate;
didodecyl naphthalene-1,8-dicarboxylate;
ditetradecyl naphthalene-1,8-dicarboxylate;
dihexadecyl naphthalene-1,8-dicarboxylate;
dioctadecyl naphthalene-1,8-dicarboxylate;
diicosyl naphthalene-1,8-dicarboxylate;
didocosyl naphthalene-1,8-dicarboxylate;
ditetracosyl naphthalene-1,8-dicarboxylate;
octyl decyl naphthalene-1,8-dicarboxylate;
octyl dodecyl naphthalene-1,8-dicarboxylate;
octyl tetradecyl naphthalene-1,8-dicarboxylate;
octyl hexadecyl naphthalene-1,8-dicarboxylate;
octyl octadecyl naphthalene-1,8-dicarboxylate;
octyl icosyl naphthalene-1,8-dicarboxylate;
octyl docosyl naphthalene-1,8-dicarboxylate;
octyl tetracosyl naphthalene-1,8-dicarboxylate;
decyl dodecyl naphthalene-1,8-dicarboxylate;

decyl tetradecyl naphthalene-1,8-dicarboxylate;
decyl hexadecyl naphthalene-1,8-dicarboxylate;
decyl octadecyl naphthalene-1,8-dicarboxylate;
decyl icosyl naphthalene-1,8-dicarboxylate;
decyl docosyl naphthalene-1,8-dicarboxylate;
decyl tetracosyl naphthalene-1,8-dicarboxylate;
dodecyl tetradecyl naphthalene-1,8-dicarboxylate;
dodecyl hexadecyl naphthalene-1,8-dicarboxylate;
dodecyl octadecyl naphthalene-1,8-dicarboxylate;
dodecyl icosyl naphthalene-1,8-dicarboxylate;
dodecyl docosyl naphthalene-1,8-dicarboxylate;
dodecyl tetracosyl naphthalene-1,8-dicarboxylate;
tetradecyl hexadecyl naphthalene-1,8-dicarboxylate;
tetradecyl octadecyl naphthalene-1,8-dicarboxylate;
tetradecyl icosyl naphthalene-1,8-dicarboxylate;
tetradecyl docosyl naphthalene-1,8-dicarboxylate;
tetradecyl tetracosyl naphthalene-1,8-dicarboxylate;
hexadecyl octadecyl naphthalene-1,8-dicarboxylate;
hexadecyl icosyl naphthalene-1,8-dicarboxylate;
hexadecyl docosyl naphthalene-1,8-dicarboxylate;
hexadecyl tetracosyl naphthalene-1,8-dicarboxylate;
octadecyl icosyl naphthalene-1,8-dicarboxylate;
octadecyl docosyl naphthalene-1,8-dicarboxylate;
octadecyl tetracosyl naphthalene-1,8-dicarboxylate;
icosyl docosyl naphthalene-1,8-dicarboxylate;
icosyl tetracosyl naphthalene-1,8-dicarboxylate;
docosyl tetracosyl naphthalene-1,8-dicarboxylate;
bis(2-ethylhexyl) naphthalene-1,8-dicarboxylate;
Bis(2-butyloctyl) naphthalene-1,8-dicarboxylate;
bis(2-hexyldecyl) naphthalene-1,8-dicarboxylate;
bis(2-octyldodecyl) naphthalene-1,8-dicarboxylate;
bis(2-decyltetradecyl) naphthalene-1,8-dicarboxylate;
2-ethylhexyl 2-butyloctyl naphthalene-1,8-dicarboxylate;
2-ethylhexyl 2-hexyldecyl naphthalene-1,8-dicarboxylate;
2-ethylhexyl 2-octyldodecyl naphthalene-1,8-dicarboxylate;
2-ethylhexyl 2-decyltetradecyl naphthalene-1,8-dicarboxylate;
2-butyloctyl 2-hexyldecyl naphthalene-1,8-dicarboxylate;
2-butyloctyl 2-octyldocecyl naphthalene-1,8-dicarboxylate;
2-butyloctyl 2-decyltetradecyl naphthalene-1,8-dicarboxylate;
2-hexyldecyl 2-octyldodecyl naphthalene-1,8-dicarboxylate;
2-hexyldecyl 2-decyltetradecyl naphthalene-1,8-dicarboxylate; and
2-octyldodecyl 2-decyltetradecyl naphthalene-1,8-dicarboxylate.

The lubricating oil base stock of the present disclosure desirably has a KV100 in the range from k1 to k2 cSt, where k1 and k2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, as long as k1<k2. Preferably k1=6.0, and k2=30.0. Therefore, the base stock of the present disclosure has a relatively "low" viscosity at the normal operating temperature of an internal combustion engine lubricating oil.

The lubricating oil base stock of the present disclosure desirably has a viscosity index in the range from v1 to v2, where v1 and v2 can be, independently, 0, 10, 20, 40, 50, 60, 80, 100, 120, 140, 150, 160, 180, 200, 220, 240, 250, 260, 280, or 300, as long as v1<v2. Preferably v1=30, v2=200; more preferably v1=40, v2=150.

The base stock of the present disclosure desirably has a NV value in the range from n1 to n2 wt %, where n1 and n2 can be, independently, 0, 0.1, 0.5, 1, 2, 3, 4, 5, 6, 7, 8, 9, 10, 11, 12, 13, 14, 15, 16, 17, 18, 19, or 20, as long as n1<n2. Preferably, n1=1, and n2=16. In general, for the same type of naphthalene-1,8-dicarboxylate ester base stock, the larger the molecular weight of the molecule, the lower the NV value. For engine oils and base stocks for them, typically a low NV value is preferred, all other parameters held equal.

The base stock of the present disclosure desirably have an aniline point less than 30, more preferably less than 25, still more preferably less than 20, still more preferably less than 15.

The naphthalene-1,8-dicarboxylate ester base stock of the present disclosure can be used as a primary base stock or a co-base stock in any lubricating oil formulation. Preferably, the naphthalene-1,8-dicarboxylate ester base stock of the present disclosure is used as a co-base stock in conjunction with a second base stock designated as a primary base stock. In certain applications, it may be desirable to include two or even more additional base stocks in the lubricating oil formulation, in addition to the naphthalene-1,8-dicarboxylate ester base stock of the present disclosure. For the convenience of description, the naphthalene-1,8-dicarboxylate ester base stock is merely referred to as a generic base stock herein, regardless of its primary base stock or co-base stock designation.

The naphthalene-1,8-dicarboxylate ester base stocks of the present disclosure are preferably used for formulating automobile engine lubricating oils, preferably those meeting the SAE J300 classification standards. However, it is contemplated that the base stocks of the present disclosure may be used to formulate other lubricating oils (e.g., automobile drive-line oils, industrial lubricating oils, gear oils, greases, and the like), heat transfer oils (e.g., transformer oils), hydraulic power transfer oils, processing oils, and the like.

III. Method for Making Naphthalene-1,8-Dicarboxylate Compounds and Lubricating Oil Base Stock Comprising the Same One aspect of the present disclosure relates to a method for making a lubricating oil base stock comprising a compound having the following formula (F-I):

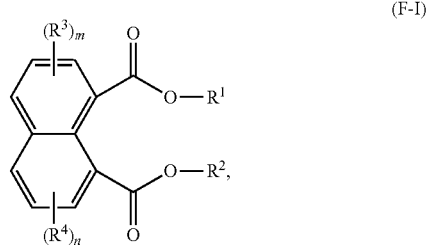

wherein:
$R^1$ and $R^2$ each are independently a C1-C32 linear or branched alkyl group;
$R^3$ and $R^4$ are each independently at each occurrence a C1-C20 alkyl group, and
m and n are independently 0, 1, 2, or 3,
the method comprising:
reacting an acid having a formula (F-IV) and/or an anhydride having a formula (F-V) below with one or more alcohols having a formula $R^1$—OH and/or $R^2$—OH in the presence of a catalyst and a solvent to obtain a reaction mixture:

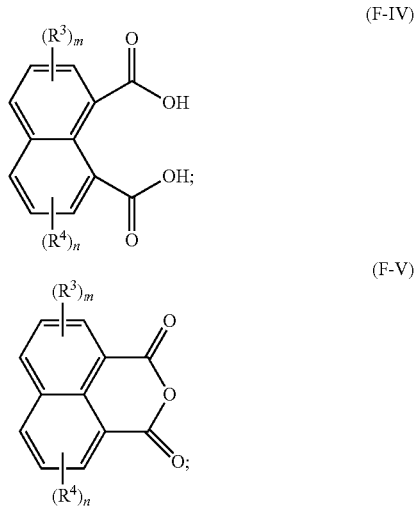

and obtaining at least a portion of the lubricating oil base stock from the reaction mixture.

It is highly desirable that the acid/anhydride used in the reaction are those of a single acid, although those of multiple acids can be used as well. To that end, the acid and/or anhydride of naphthalene-1,8-dicarboxylic acid (corresponding to the compound of formula (F-IV) and (F-V) wherein m and n are zero) is particular preferred due to its cost and availability. However, those acid/anhydride of formula (F-IV) and (F-V) where at least one of m and n is not zero, and at least one of $R^3$ and $R^4$ is a long chain alkyl group, such as a linear alkyl group or a 1-substituted linear alkyl group comprising at least 6 carbon atoms therein can be advantageous in that the long $R^3$ and $R^4$ chains may enhance the blending compatibility of the base stock.

It is highly desirable that a single alcohol (i.e., where $R^1$ in alcohol $R^1$—OH and $R^2$ in alcohol $R^2$—OH are identical) is used in the reaction. In such case, if an acid/anhydride of a single acid is used, a high-purity ester compound having a formula (F-I) can be obtained and used as a lubricating oil base stock. This is illustrated in Examples 1, 2, 3A and 3B in the present disclosure.

It is also contemplated that multiple alcohols (i.e., where $R^1$ in alcohol $R^1$—OH and $R^2$ in alcohol $R^2$—OH are different, $R^1$—OH and $R^2$—OH being two of the multiple alcohols) can be used in the reaction. In the case where two different alcohols and the acid/anhydride of a single acid are used in the reaction, the reaction mixture will comprise three different ester compounds: a first ester compound of formula (F-I); a second ester compound of formula (F-I) except that $R^2$ is replaced by $R^1$; and a third ester compound of formula (F-I) except that $R^1$ is replaced by $R^2$. The ratio between and among the quantities of the first, second, and third ester compounds can change as a function of the ratio between the quantities of alcohol $R^1$—OH and alcohol $R^2$—OH. In certain situations, where a mixture of alcohols having similar molecular weights and structures can be procured at a lower cost than a pure alcohol compound, this embodiment can be highly economic to produce a mixture of ester compounds with similar molecular structures, molecular weights, and properties suitable as a lubricating oil base stock product.

In a particularly desirable embodiment, $R^1$ and $R^2$ are the same or different, and at least one of $R^1$ and $R^2$ is a branched alkyl group represented by the following formula (F-II):

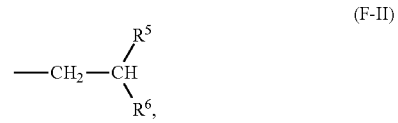

where $R^5$ and $R^6$ are independently a C1-C29 linear or branched alkyl group. In this embodiment, at least one of the alcohols used can be desirably a Guerbet alcohol.

Guerbet alcohols can be produced by converting one or more primary alcohol through a Guerbet reaction. A Guerbet reaction of a single alcohol can be illustrated as follows:

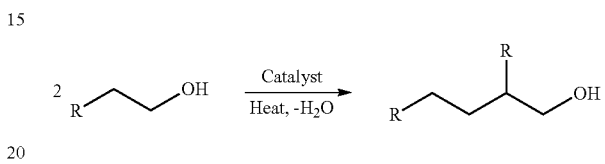

In the reaction above, the Guerbet reaction from a primary alcohol results in a beta-branched alcohol (i.e., a Guerbet alcohol), where the two groups (R— and R—$CH_2CH_2$—) connected to the beta carbon atom differ in total carbon atoms contained therein by two (2).

As described above, when a Guerbet alcohol is used to make the base stock comprising a naphthalene-1,8-dicarboxylate ester compound, it is highly desirable to use a single Guerbet alcohol to obtain a single naphthalene-1,8-dicarboxylate ester compound, which can then be used as a base stock or mixed with other components to form a base stock. It is possible to make an ester mixture base stock by using two or more different Guerbet alcohols. It is also possible to make an ester mixture by using a mixture of one or more Guerbet alcohol and one or more non-Guerbet alcohol such as linear alcohols. Using mixtures of alcohols having similar molecular weights and molecular structures that can be produced simultaneously and difficult to separate can be highly economical, to the extent the resulting ester compounds also have similar molecular weights, molecular structures and properties.

The catalyst used in the reaction can be an acid, desirably a strong acid. Non-limiting examples of such acid are: p-toluenesulfonic acid monohydride (PTSA), titanium isopropoxide or sulfuric acid.

The reaction can be advantageously carried out in the presence of a solvent. The specific solvent used is not critical as long as it is inert in the reaction. Non-limiting examples of the solvent are the following and mixtures thereof: benzene, toluene, xylenes, ethylbenzene, n-pentane and isomers thereof, n-hexane and isomers thereof, n-heptane and isomers thereof, n-octane and isomers thereof, and cyclohexane and saturated isomers thereof. Preferred examples of solvents are the following and mixtures thereof: toluene, n-hexane and isomers thereof, cyclohexane and saturated isomers thereof, ethylbenzene, and any xylene and mixtures thereof.

The reaction mixture typically comprises the intended ester product(s), water, unreacted acid/anhydride and alcohol, and byproducts such as ethers, and esters of the acid catalyst. Continuous removal of water from the reaction system can result in higher yield of the ester compounds. Components in the reaction mixture having a boiling point lower than the intended naphthalene-1,8-dicarboxylate ester can be removed by vacuum. Purification methods such as solvent extraction, chromatography, and the use of sorbents can be carried out to remove byproducts from reaction mixture to finally obtain one compound of formula (F-I), or a mixture of multiple compounds of formula (F-I), depending on the reactants used, which can be used as a base stock product, or combined with other, similar compounds to form a base stock product.

IV. Lubricating Oil Compositions Containing the Naphthalene-1,8-Dicarboxylate Ester Base Stock IV.1 General The naphthalene-1,8-dicarboxylate ester base stocks of this disclosure are useful in formulating lubricating oils. The oil composition of the first aspect of the present disclosure summarized above can be a portion or the entirety of a lubricating oil formulation ready to be used in its intended application. Thus, the oil composition can be, among others: (i) a mixture of the naphthalene-1,8-dicarboxylate ester base stock and the remainder of the formulation absent the naphthalene-1,8-dicarboxylate ester base stock; (ii) a mixture of the naphthalene-1,8-dicarboxylate ester base stock with one or more other base stocks contained in the lubricating oil formulation absent the additive components in the lubricating oil formulation; (iii) a mixture of the naphthalene-1,8-dicarboxylate ester base stock and all other base stocks contained in the lubricating oil formulation but absent any additive components that may be present in the lubricating oil formulation; (iv) a mixture of the naphthalene-1,8-dicarboxylate ester base stock and one or more other base stocks, but not all the other base stocks, contained in the lubricating oil formulation, and at least a portion of the additive components contained in the lubricating oil formulation; and (v) a mixture of the naphthalene-1,8-dicarboxylate ester base stock and all additive components contained in the lubricating oil formulation, but no other base stocks contained in the lubricating oil formulation.

Therefore, to make a final lubricating oil formulation of a product, one may add additional components, such as other base stocks, additional quantities of the materials already present in the oil composition, additive components, and the like, to the oil composition. A particularly preferred embodiment of the oil composition of the present disclosure; however, is a lubricating oil formulation.

The naphthalene-1,8-dicarboxylate ester base stock can be present in the lubricating oil formulation of this disclosure in an amount from about c1 to c2 wt %, based on the total weight of the oil composition, where c1 and c2 can be, independently, 1, 2, 3, 4, 5, 6, 7, 8, 9, 10, 15, 20, 25, 30, 35, 40, 45, 50, 60, 70, 80, or 90, as long as c1<c2. Preferably C1=1 and C2=50; more preferably c1=2, and c2=30; still more preferably c1=3, and c2=15. In general, it is desirable that the oil composition contains the naphthalene-1,8-dicarboxylate ester base stock as a co-base stock.

Owing to the high polarity of the naphthalene-1,8-dicarboxylate ester base stocks resulting from the naphthalene group and the two ester groups in their molecular structures, the lubricating oil compositions of the present disclosure can have an improved polar additive and sludge solvency and dispersancy compared to other lubricating oil compositions free of ester-type base stocks. In addition, a lubricating oil formulation including a naphthalene-1,8-dicarboxylate ester base stock can impart improved seal compatibility compared to formulations free of ester-type base stocks.

IV.2 Other Base Stocks Useful in the Lubricating Oil

A wide range of lubricating oil base stocks known in the art can be used in conjunction with the naphthalene-1,8-dicarboxylate ester base stock in the lubricating oil formulations of the present disclosure, as a primary base stock or a co-base stock. Such other base stocks can be either derived from natural resources or synthetic, including un-refined, refined, or re-refined oils. Un-refined oil base stocks include shale oil obtained directly from retorting operations, petroleum oil obtained directly from primary distillation, and ester oil obtained directly from a natural source (such as plant matters and animal tissues) or directly from a chemical esterification process. Refined oil base stocks are those un-refined base stocks further subjected to one or more purification steps such as solvent extraction, secondary distillation, acid extraction, base extraction, filtration, and percolation to improve at least one lubricating oil property. Re-refined oil base stocks are obtained by processes analogous to refined oils but using an oil that has been previously used as a feed stock.

API Groups I, II, III, IV and V are broad categories of base stocks developed and defined by the American Petroleum Institute (API Publication 1509; www.API.org) to create guidelines for lubricating oil base stocks. Group I base stocks generally have a viscosity index of from about 80 to 120 and contain greater than about 0.03% sulfur and less than about 90% saturates. Group II base stocks generally have a viscosity index of from about 80 to 120, and contain less than or equal to about 0.03% sulfur and greater than or equal to about 90% saturates. Group III base stocks generally have a viscosity index greater than about 120 and contains less than or equal to about 0.03% sulfur and greater than about 90% saturates. Group IV includes polyalphaolefins (PAO). Group V base stocks include base stocks not included in Groups I to IV. The table below summarizes properties of each of these five groups.

| Base Stock Properties | | | |
|---|---|---|---|
| | Saturates | Sulfur | Viscosity Index |
| Group I | Higher than 90 and/or | Higher than 0.03% and | At least 80 and at most 120 |
| Group II | Higher than 90 and | At most 0.03% and | At least 80 and at most 120 |
| Group III | At least 90 and | At most 0.03% and | At least 120 |
| Group IV | | PAO products | |
| Group V | All other products not included in Groups I, II, III, and IV | | |

Natural oils include animal oils (e.g. lard), vegetable oils (e.g., castor oil), and mineral oils. Animal and vegetable oils possessing favorable thermal oxidative stability can be used. Of the natural oils, mineral oils are preferred. Mineral oils vary widely as to their crude source, e.g., as to whether they are paraffinic, naphthenic, or mixed paraffinic-naphthenic. Oils derived from coal or shale are also useful in the present disclosure. Natural oils vary also as to the method used for their production and purification, e.g., their distillation range and whether they are straight run or cracked, hydrorefined, or solvent extracted.

Group II and/or Group III base stocks are generally hydroprocessed or hydrocracked base stocks derived from crude oil refining processes.

Synthetic base stocks include polymerized and interpolymerized olefins (e.g., polybutylenes, polypropylenes, propylene isobutylene copolymers, ethylene-olefin copolymers, and ethylene-alphaolefin copolymers).

Synthetic polyalphaolefins ("PAO") base stocks are placed into Group IV. Advantageous Group IV base stocks are those made from one or more of C6, C8, C10, C12, and C14 linear alpha-olefins ("LAO"s). These base stocks can be commercially available at a wide range of viscosity, such as a KV100 in the range from 1.0 to 1,000 cSt. The PAO base stocks can be made by polymerization of the LAO(s) in the presence of Lewis-acid type catalyst or a metallocene compound-based catalyst system. High quality Group IV PAO commercial base stocks include the SpectraSyn™ and SpectraSyn Elite™ series available from ExxonMobil Chemical Company having an address at 4500 Bayway Drive, Baytown, Tex. 77520, U.S.A.

All other synthetic base stocks, including but not limited to alkyl aromatics and synthetic esters are in Group V.

Additional esters not in the naphthalene-1,8-dicarboxylate ester category in a minor amount may be useful in the lubricating oil formulations of this disclosure. Additive solvency and seal compatibility characteristics may be imparted by the use of esters such as the esters of dibasic acids with monoalkanols and the polyol esters of monocarboxylic acids. Esters of the former type include, e.g., the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc. Useful ester-type Group V base stock include the Esterex™ series commercially available from ExxonMobil Chemical Company.

One or more of the following may be used as a base stock in the lubricating oil of the present disclosure as well: (1) one or more Gas-to-Liquids (GTL) materials; and (2) hydrodewaxed, hydroisomerized, solvent dewaxed, or catalytically dewaxed base stocks derived from synthetic wax, natural wax, waxy feeds, slack waxes, gas oils, waxy fuels, hydrocracker bottoms, waxy raffinate, hydrocrackate, thermal crackates, foots oil, and waxy materials derived from coal liquefaction or shale oil. Such waxy feeds can be derived from mineral oils or non-mineral oil processing or can be synthetic (e.g., Fischer-Tropsch feed stocks). Such base stocks preferably comprise linear or branched hydrocarbyl compounds of C20 or higher, more preferably C30 or higher.

The lubricating oil formulations of the present disclosure can comprise one or more Group I, II, III, IV, or V base stocks in addition to the naphthalene-1,8-dicarboxylate ester base stock. Preferably, Group I base stocks, if any, are present at a relatively low concentration if a high quality lubricating oil is desired. Group I base stocks may be introduced as a diluent of an additive package at a small quantity. Groups II and III base stocks can be included in the lubricating oil formulations of the present disclosure, but preferably only those with high quality, e.g., those having a VI from 100 to 120. Group IV and V base stocks, preferably those of high quality, are desirably included into the lubricating oil formulations of the present disclosure.

IV.3 Lubricating Oil Additives

The formulated lubricating oil useful in the present disclosure may additionally contain one or more of the commonly used lubricating oil performance additives including but not limited to dispersants, detergents, viscosity modifiers, antiwear additives, corrosion inhibitors, rust inhibitors, metal deactivators, extreme pressure additives, anti-seizure agents, wax modifiers, viscosity modifiers, fluid-loss additives, seal compatibility agents, lubricity agents, anti-staining agents, chromophoric agents, defoamants, demulsifiers, densifiers, wetting agents, gelling agents, tackiness agents, colorants, and others. For a review of many commonly used additives and the quantities used, see: (i) Klamann in Lubricants and Related Products, Verlag Chemie, Deerfield Beach, Fla.; ISBN 0-89573-177-0; (ii) "Lubricant Additives," M. W. Ranney, published by Noyes Data Corporation of Parkridge, N J (1973); (iii) "Synthetics, Mineral Oils, and Bio-Based Lubricants," Edited by L. R. Rudnick, CRC Taylor and Francis, 2006, ISBN 1-57444-723-8; (iv) "Lubrication Fundamentals", J. G. Wills, Marcel Dekker Inc., (New York, 1980); (v) Synthetic Lubricants and High-Performance Functional Fluids, 2nd Ed., Rudnick and Shubkin, Marcel Dekker Inc., (New York, 1999); and (vi) "Polyalphaolefins," L. R. Rudnick, Chemical Industries (Boca Raton, Fla., United States) (2006), 111 (Synthetics, Mineral Oils, and Bio-Based Lubricants), 3-36. Reference is also made to: (a) U.S. Pat. No. 7,704,930 B2; (b) U.S. Pat. No. 9,458,403 B2, Column 18, line 46 to Column 39, line 68; (c) U.S. Pat. No. 9,422,497 B2, Column 34, line 4 to Column 40, line 55; and (d) U.S. Pat. No. 8,048,833 B2, Column 17, line 48 to Column 27, line 12, the disclosures of which are incorporated herein in their entirety. These additives are commonly delivered with varying amounts of diluent oil that may range from 5 wt % to 50 wt % based on the total weight of the additive package before incorporation into the formulated oil. The additives useful in this disclosure do not have to be soluble in the lubricating oil formulations. Insoluble additives in oil can be dispersed in the lubricating oil formulations of this disclosure.

When lubricating oil formulations contain one or more of the additives discussed above, the additive(s) are blended into the oil composition in an amount sufficient for it to perform its intended function.

It is noted that many of the additives are shipped from the additive manufacturer as a concentrate, containing one or more additives together, with a certain amount of base oil diluents.

Examples of techniques that can be employed to characterize the naphthalene-1,8-dicarboxylate ester base stock described above include, but are not limited to, analytical gas chromatography, nuclear magnetic resonance, thermogravimetric analysis (TGA), inductively coupled plasma mass spectrometry, differential scanning calorimetry (DSC), and volatility and viscosity measurements.

The present invention is further illustrated by the following non-limiting examples.

EXAMPLES

Example 1: Didecyl Naphthalene-1,8-dicarboxylate

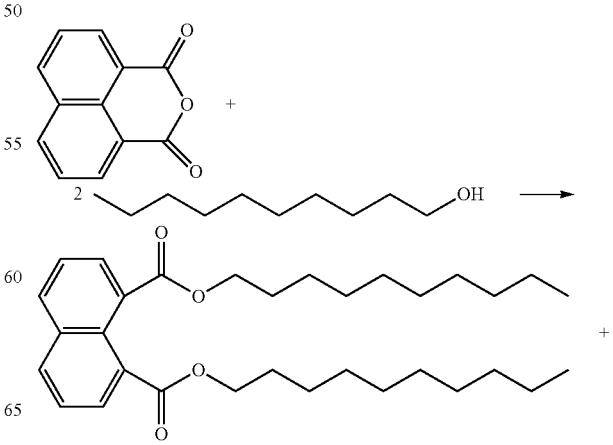

Into a 1000-mL 3-neck round bottom fitted with a Dean-Stark apparatus was charged with 1,8-naphthalic anhydride (10.0 grams, 50.46 mmol), 1-decanol (300 mL, 1571 mmol), xylenes (200 mL), and p-toluenesulfonic acid monohydrate (0.96 gram, 5.05 mmol). The solution was refluxed under a dry nitrogen atmosphere for 48 hours after which only a trace of anhydride was detected by TLC (thin-layer chromatography, 20% EtOAc/hexanes). The reaction mixture was concentrated under high vacuum (<1 Torr, 133 Pascal) to 27.73 grams crude product as an amber colored oil that was ~85% pure by gas chromatography (approximately 94% yield). Impurities identified by $^1$H NMR included didecyl ether (major) and decyl p-toluenesulfonate. The crude material was combined with other preparations and purified by automated column chromatography (2×) in 3-5 grams batches producing approximately 1.5-3 grams of purified material (99+% by $^1$H NMR) each run as a light yellow oil (Biotage, 100 grams SNAP ultra, 0-5% EtOAc/hexanes). To further reduce color the accumulated purified product (23.5 grams) was dissolved in hexane (200 mL), stirred with decolorizing carbon (2 grams) for 2 hours, filtered through a silica gel plug, and concentrated under high vacuum (<1 Torr, 133 Pascal) at 105° C. for 2 hours to remove all volatiles. Proton NMR spectrum: $^1$H NMR (CD$_2$Cl$_2$, 400 MHz) δ 8.03 (dd, 2H, ArH), δ 7.98 (m, 2H, ArH), δ 7.56 (appt, 2H, ArH), δ 4.26 (t, 4H, —OCH$_2$—), δ 1.78 (m, 4H, —CH$_2$), δ 1.5-1.2 (m, 28H, —CH$_2$), δ 0.88 (t, 6H, —CH$_3$).

Example 2: Di(2-butyloctyl) Naphthalene-1,8-Dicarboxylate

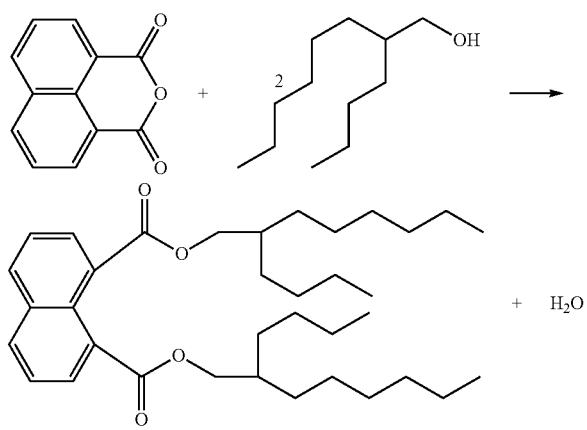

A mixture of 1,8-naphthalic anhydride (10.0 grams, 50.46 mmol), 2-butyl-1-octanol (28.21 grams, 151.4 mmol), sulfuric acid (0.5 ml, concentrated), and xylene (130 ml) was heated to reflux under N$_2$ for 24 hours. The by-product water was removed from the reaction by using Dean-Stark trap. Then the reaction mixture was washed with H$_2$O, aqueous Na$_2$CO$_3$, H$_2$O, and brine; dried over MgSO$_4$, and concentrated to give brown liquid crude product, which was further purified by silica gel column chromatography to give brown viscous product 18.2 grams (pure). The structure was characterized by $^1$H and $^{13}$C NMR spectra: $^1$H NMR (CDCl$_3$, 400 MHz) δ 7.97 (m, 4H, ArH), δ 7.53 (t, 2H, ArH), δ 4.22 (d, 4H, —OCH$_2$—), δ 1.80 (m, 2H, —CH—), δ 1.46-1.26 (m, 32H, —CH$_2$—), δ 0.87 (m, 12H, —CH$_3$). $^{13}$C NMR (CDCl$_3$, 100 MHz) δ 169.1, 134.6, 132.3, 130.6, 129.9, 127.8, 125.4, 68.3, 37.6 32.1, 31.5, 31.2, 29.9, 29.1, 26.9, 23.2, 22.9, 14.3, 14.26. $^{13}$C NMR (CDCl$_3$, 100 MHz, DEPT-135) δ 132.1, 129.7, and 125.2 (CH); δ 68.1 (CH$_2$); δ 37.4 (CH); δ 31.9, 31.3, 31.0, 29.7, 28.9, 26.7, 23.0, and 22.7 (CH$_2$); δ 14.1 and 14.08 (CH$_3$).

Example 3A: Di(2-hexyldecyl) Naphthalene-1,8-dicarboxylate, Catalyst: p-TsOH

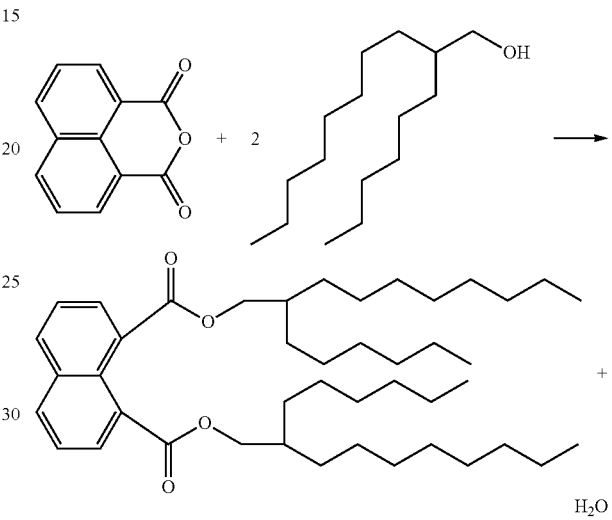

A mixture of 1,8-naphthalic anhydride (10.0 grams, 50.46 mmol), 2-hexyl-1-decanol (26.9 grams, 111.01 mmol), p-toluenesulfonic acid monohydrate (0.96 gram, 5.05 mmol), and xylene (130 ml) was heated to reflux under N$_2$ for 24 hours. The by-product water was removed from the reaction by using Dean-Stark trap. Then the reaction mixture was washed with aqueous Na$_2$CO$_3$, H$_2$O, and brine; dried over MgSO$_4$, and concentrated to give light brown liquid crude product, which was further purified by silica gel column chromatography to give light yellow viscous product 23.95 grams (contained residue of p-TsOH). The structure was characterized by $^1$H-NMR spectrum: $^1$H NMR (CDCl$_3$, 400 MHz) δ 7.97 (m, 4H, ArH), δ 7.53 (t, 2H, ArH), δ 4.22 (d, 4H, —OCH$_2$—), δ 1.80 (m, 2H, —CH—), δ 1.43-1.17 (m, 48H, —CH$_2$—), δ 0.87 (m, 12H, —CH$_3$).

Example 3B: Di(2-hexyldecyl) Naphthalene-1,8-dicarboxylate, Catalyst: H$_2$SO$_4$

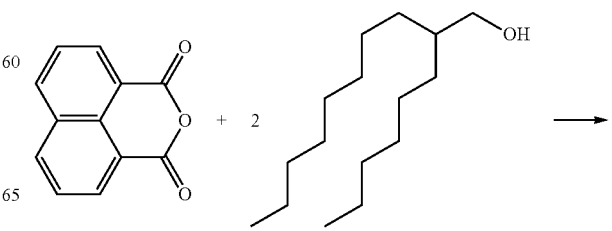

-continued

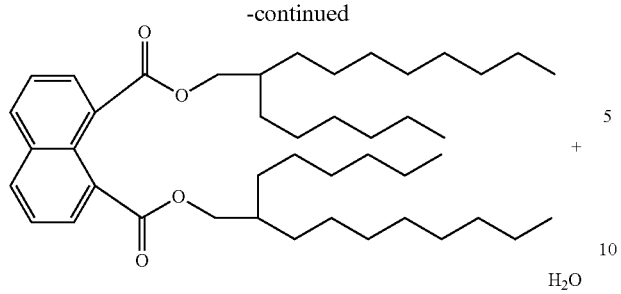

+

$H_2O$

A mixture of 1,8-naphthalic anhydride (10.0 grams, 50.46 mmol), 2-hexyl-1-decanol (36.7 grams, 151.4 mmol), sulfuric acid (0.5 ml, concentrated), and xylene (130 ml) was heated to reflux under $N_2$ for 15 hours. The by-product water was removed from the reaction by using Dean-Stark trap. Then the reaction mixture was washed with $H_2O$, aqueous $Na_2CO_3$, $H_2O$, and brine; dried over $MgSO_4$, and concentrated to give brown liquid crude product, which was further purified by silica gel column chromatography to give amber color viscous product 17.74 grams (pure). The structure was characterized by $^1H$ and $^{13}C$ NMR spectra: $^1H$ NMR ($CDCl_3$, 400 MHz) δ 7.97 (d, 4H, ArH), δ 7.52 (t, 2H, ArH), δ 4.22 (d, 4H, —$OCH_2$—), δ 1.80 (m, 2H, —CH—), δ 1.46-1.26 (m, 48H, —$CH_2$—), δ 0.87 (m, 12H, —$CH_3$). $^{13}C$ NMR ($CDCl_3$, 100 MHz) δ 169.1, 134.6, 132.2, 130.6, 129.9, 127.8, 125.3, 68.3, 37.6 32.1, 32.0, 31.5, 30.2, 29.84, 29.78, 29.5, 26.92, 26.88, 22.9, 22.8, 14.3. $^{13}C$ NMR ($CDCl_3$, 100 MHz, DEPT-135) δ 132.2, 129.9, and 125.3 (CH); δ 68.3 ($CH_2$); δ 37.6 (CH); δ 32.1, 32.0, 31.5, 30.2, 29.84, 29.78, 29.5, 26.92, 26.88, 22.9, and 22.8 ($CH_2$); δ 14.3 ($CH_3$).

The ester products of Examples 1, 2, 3A, and 3B were then measured for lubricant properties. Data are included in TABLE I below. Included in TABLE I are also properties of two commercial ester Group V base stock products available from ExxonMobil Chemical Company having an address at 4500 Bayway Drive, Baytown, Tex. 77520, U.S.A. The Noack volatility ("NV") values were measured by thermogravimetric analysis ("TGA") based Noack or regular Noack as determined by ASTM D5800. All of the esters of Examples 1, 2, 3A, and 3B exhibit KV100, KV40, and viscosity index similar to the two commercial products, indicating they are suitable as a high-quality low-viscosity base stock for lubricant formulations. Due to the nature of esters, they are expected to have higher polarity than group IV PAO-type base stocks, and therefore can impart desired solvency and dispersancy of polar additives and sludge formed during the service life of the lubricating oil service life, providing better protection of the engine or other equipment or longer life of the oil formulation.

What is claimed is:

1. A lubricating oil base stock comprising a compound having the following formula (F-I):

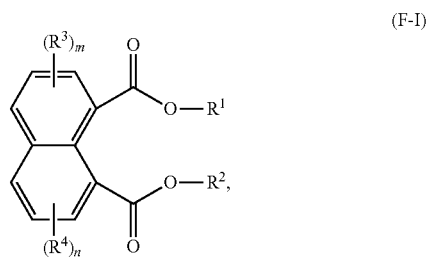

wherein:
$R^1$ and $R^2$ are each independently a C1 to C32 linear or branched alkyl group and at least one of $R^1$ and $R^2$ is a branched alkyl group represented by the following formula (F-II):

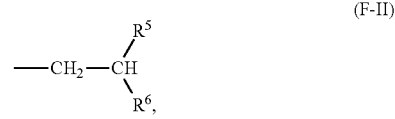

where $R^5$ and $R^6$ are each independently a C1 to C29 linear or branched alkyl group;
$R^3$ and $R^4$ are independently at each occurrence a C1 to C20 alkyl group; and
m and n are independently 0, 1, 2, or 3.

2. The lubricating oil base stock of claim 1, wherein both m and n are zero.

3. The lubricating oil base stock of claim 1, wherein $R^1$ and $R^2$ are identical.

4. The lubricating oil base stock of claim 1, wherein $R^1$ and $R^2$ are each independently a C8 to C24 linear or branched alkyl group.

5. The lubricating oil base stock of claim 1, wherein $R^5$ and $R^6$ are each independently a C2 to C22 linear or branched alkyl group.

6. The lubricating oil base stock of claim 1, wherein $R^5$ and $R^6$ are linear alkyl groups.

7. The lubricating oil base stock of claim 5, wherein the difference in total number of carbon atoms contained in $R^5$ and $R^6$ is two (2).

8. The lubricating oil base stock of claim 1, consisting essentially of one or more compounds having formula (I) where $R^1$ and $R^2$ are linear alkyl groups.

TABLE I

| Example No. | Ester | KV100 (cSt) | KV40 (cSt) | Viscosity Index | NV (%) |
|---|---|---|---|---|---|
| 1 | Didecyl naphthalene-1,8-dicarboxylate | 10.4 | 107.8 | 70 | 2.0 (TGA) |
| 2 | Bis(2-butyloctyl) naphthalene-1,8-dicarboxylate | 12.0 | 152.8 | 53 | — |
| 3A | Bis(2-hexyldecyl) naphthalene-1,8-dicarboxylate | 12.2 | 129.6 | 82 | — |
| 3B | Bis(2-hexyldecyl) naphthalene-1,8-dicarboxylate | 14.7 | 170.8 | 82 | — |
| Esterex | Esterex Trimellitate ™ 101 | 9.8 | 89.0 | 86 | 1.8 |
| Esterex | Esterex Trimellitate ™ 111 | 11.9 | 124.0 | 81 | 1.4 |

9. The lubricating oil base stock of claim 1, consisting essentially of a mixture of:
  one or more compounds having formula (I) where $R^1$ and $R^2$ are linear alkyl groups; and
  one or more compounds having formula (I) where at least one of $R^1$ and $R^2$ is represented by formula (F-II).

10. The lubricating oil base stock of claim 1, comprising one or more of the following compounds:
  bis(2-ethylhexyl) naphthalene-1,8-dicarboxylate;
  bis(2-butyloctyl) naphthalene-1,8-dicarboxylate;
  bis(2-hexyldecyl) naphthalene-1,8-dicarboxylate;
  bis(2-octyldocecyl) naphthalene-1,8-dicarboxylate;
  bis(2-decyltetradecyl) naphthalene-1,8-dicarboxylate;
  2-ethylhexyl 2-butyloctyl naphthalene-1,8-dicarboxylate;
  2-ethylhexyl 2-hexyldecyl naphthalene-1,8-dicarboxylate;
  2-ethylhexyl 2-octyldodecyl naphthalene-1,8-dicarboxylate;
  2-ethylhexyl 2-decyltetradecyl naphthalene-1,8-dicarboxylate;
  2-butyloctyl 2-hexyldecyl naphthalene-1,8-dicarboxylate;
  2-butyloctyl 2-octyldodecyl naphthalene-1,8-dicarboxylate;
  2-butyloctyl 2-decyltetradecyl naphthalene-1,8-dicarboxylate;
  2-hexyldecyl 2-octyldodecyl naphthalene-1,8-dicarboxylate;
  2-hexyldecyl 2-decyltetradecyl naphthalene-1,8-dicarboxylate; and
  2-octyldodecyl 2-decyltetradecyl naphthalene-1,8-dicarboxylate.

11. The lubricating oil base stock of claim 1, consisting essentially of one or more of the following compounds:
  bis(2-ethylhexyl) naphthalene-1,8-dicarboxylate;
  bis(2-butyloctyl) naphthalene-1,8-dicarboxylate;
  bis(2-hexyldecyl) naphthalene-1,8-dicarboxylate;
  bis(2-octyldocecyl) naphthalene-1,8-dicarboxylate;
  bis(2-decyltetradecyl) naphthalene-1,8-dicarboxylate;
  2-ethylhexyl 2-butyloctyl naphthalene-1,8-dicarboxylate;
  2-ethylhexyl 2-hexyldecyl naphthalene-1,8-dicarboxylate;
  2-ethylhexyl 2-octyldocecyl naphthalene-1,8-dicarboxylate;
  2-ethylhexyl 2-decyltetradecyl naphthalene-1,8-dicarboxylate;
  2-butyloctyl 2-hexyldecyl naphthalene-1,8-dicarboxylate;
  2-butyloctyl 2-octyldocecyl naphthalene-1,8-dicarboxylate;
  2-butyloctyl 2-decyltetradecyl naphthalene-1,8-dicarboxylate;
  2-hexyldecyl 2-octyldocecyl naphthalene-1,8-dicarboxylate;
  2-hexyldecyl 2-decyltetradecyl naphthalene-1,8-dicarboxylate; and
  2-octyldocecyl 2-decyltetradecyl naphthalene-1,8-dicarboxylate.

12. The lubricating oil base stock of claim 1, having a kinematic viscosity at 100° C. as determined by ASTM D445 ("KV100") in the range from 4 to 40 cSt.

13. A lubricating oil composition comprising a first base stock, a second base stock different from the first base stock, and an additive, wherein the first base stock comprises a lubricating oil base stock of claim 1.

14. A method for making a lubricating oil base stock comprising a compound having the following formula (F-I):

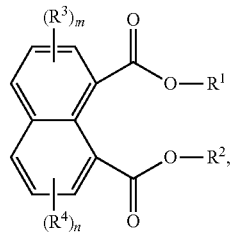

wherein:
$R^1$ and $R^2$ are each independently a C1 to C32 linear or branched alkyl group and at least one of $R^1$ and $R^2$ is a branched alkyl group represented by the following formula (F-II):

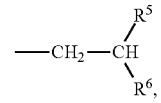

where $R^5$ and $R^6$ are independently a C1 to C29 linear or branched alkyl group;
$R^3$ and $R^4$ are each independently at each occurrence a C1 to C20 alkyl group, and
m and n are independently 0, 1, 2, or 3,
the method comprising:
reacting an acid having a formula (F-V) and/or an anhydride having a formula (F-VI) below with one or more alcohols having a formula $R^1$—OH and/or $R^2$—OH in the presence of a catalyst to obtain a reaction mixture:

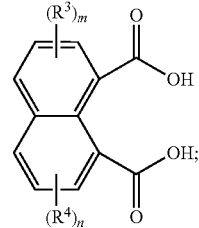

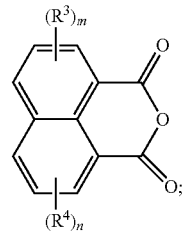

and
obtaining at least a portion of the lubricating oil base stock from the reaction mixture.

15. The process of claim 14, wherein the catalyst comprises p-toluenesulfonic acid monohydride (PTSA), titanium isopropoxide or sulfuric acid.

* * * * *